United States Patent [19]

Martan et al.

[11] Patent Number: 5,017,542

[45] Date of Patent: May 21, 1991

[54] CATALYST FOR THE OXIDATION AND AMMONOXIDATION OF α-, β-UNSATURATED HYDROCARBONS

[75] Inventors: Hans Martan; Wolf D. Mross, both of Frankenthal; Gerd-Juergen Engert, Ludwigshafen, all of Fed. Rep. of Germany

[73] Assignee: BASF Aktiengesellschaft, Ludwigshafen, Fed. Rep. of Germany

[21] Appl. No.: 391,310

[22] Filed: Aug. 9, 1989

[30] Foreign Application Priority Data

Aug. 16, 1988 [DE] Fed. Rep. of Germany ....... 3827639

[51] Int. Cl.$^5$ .................. B01J 23/78; B01J 23/84; B01J 23/88; B01J 35/02

[52] U.S. Cl. .................... 502/209; 502/210; 502/212; 502/243; 502/307; 502/313; 502/527

[58] Field of Search ............. 502/243, 527, 209, 210, 502/307, 313, 212

[56] References Cited

U.S. PATENT DOCUMENTS

| | | | |
|---|---|---|---|
| 4,052,450 | 10/1977 | Krabetz et al. | 260/533 N |
| 4,337,178 | 6/1982 | Atwood et al. | 252/466 J |
| 4,511,671 | 4/1985 | Saito et al. | 502/242 |
| 4,732,884 | 3/1988 | Sarumaru et al. | 502/243 X |

FOREIGN PATENT DOCUMENTS

| | | |
|---|---|---|
| 15565 | 9/1980 | European Pat. Off. . |
| 15569 | 9/1980 | European Pat. Off. . |
| 17000 | 9/1980 | European Pat. Off. . |
| 68192 | 12/1982 | European Pat. Off. . |
| 2249922 | 4/1974 | Fed. Rep. of Germany . |
| 3300044 | 7/1983 | Fed. Rep. of Germany . |
| 1282949 | 7/1972 | United Kingdom . |
| 1282950 | 7/1972 | United Kingdom . |

*Primary Examiner*—W. J. Shine
*Attorney, Agent, or Firm*—Oblon, Spivak, McClelland, Maier & Neustadt

[57] ABSTRACT

Catalyst particles of an active material of the general formula

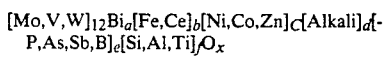

where
a is from 0.1 to 5,
b is from 0.1 to 10,
c is from 1 to 15,
d is from 0.01 to 2,
e is from 0 to 2,
f is from 0 to 30 and
x is the number of oxygen atoms required to saturate the valences of the other components, have the shape of a 3-spoked to 5-spoked wheel or of a rosette which have wall thicknesses of from 0.5 to 4 mm and a diameter of from 3 to 20 mm.

1 Claim, 2 Drawing Sheets

CATALYST FOR THE OXIDATION AND AMMONOXIDATION OF α-, β-UNSATURATED HYDROCARBONS

The present invention relates to catalyst particles consisting of an active material, as used as catalysts for the oxidation and ammonoxidation of α-,β-olefinically unsaturated hydrocarbons to the corresponding aldehydes, carboxylic acids or nitriles.

Many oxidic catalysts have been proposed for the preparation of α-,β-unsaturated aldehydes, carboxylic acids and nitriles by oxidation or ammonoxidation of olefinically unsaturated hydrocarbons in the gas phase at about 250°–450° C., frequently in the presence of steam, most of the said catalysts being derived from predominant amounts of molybdenum (and/or vanadium and/or tungsten) and minor amounts of bismuth, as well as iron (and/or cerium) and nickel and/or cobalt and/or zinc, and traces of alkali metals, preferably potassium, and additionally containing phosphorus, arsenic, antimony and boron and also (often as components of carriers) silicon, aluminum and/or titanium in oxide form. Catalysts of this type are frequently used in the form of cylinders and of rings or spheres, the catalytically active material frequently being applied in a thin layer to spherical or annular carriers. Catalyts of this type are described in, for example, German Laid-Open Application DOS 3,300,044, German Patent 2,249,922 and European Patents 15,565, 15,569, 17,000 and 68,192. The catalysts of this type are used in the oxidation or ammonoxidation reactions, in general as fixed-bed catalysts.

However, when these oxidation processes are carried out in practice, for example for the preparation of acrolein and acrylic acid by gas phase oxidation of propylene, the yields and selectivities obtained are still unsatisfactory. For example, although unsupported catalysts, i.e. catalysts whose volume is produced completely from the catalytically active material, if necessary diluted with carriers, have a high volume-specific activity, they are relatively nonselective and thus lead to further oxidation to the thermodynamically favored end products CO and $CO_2$. More favorable in this respect are coated catalysts, i.e. catalysts in which a (generally spherical) core of catalytically inactive carrier has a thin coating of the catalytically active material.

Although these have relatively good selectivity, they possess only a low volume-specific activity, since the major part of the volume is occupied by catalytically inactive carrier. They must therefore be operated at relatively high temperatures, so that the catalyst lives are adversely affected and the selectivity is not optimally utilized. Furthermore, like most of the unsupported catalysts, they frequently exhibit considerable flow resistance. However, an increase in pressure in the stated oxidation and ammonoxidation processes likewise favors the secondary reactions leading to carbon monoxide and carbon dioxide.

It is an object of the present invention to provide catalysts which simultaneously have particularly high selectivities and volume-specific activities for the gas-phase oxidation and ammonoxidation of monoolefinically unsaturated hydrocarbons to α,β-monoolefinically unsaturated aldehydes, α,β-monoolefinically unsaturated carboxylic acids and α,β-monoolefinically unsaturated nitriles.

We have found that this object is achieved by catalyst particles consisting of an active material of the general formula

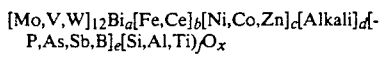

where
a is from 0.1 to 5,
b is from 0.1 to 10,
c is from 1 to 15,
d is from 0.01 to 2,
e is from 0 to 2,
f is from 0 to 30 and
x is the number of oxygen atoms required to saturate the valences of the other components, if said particles have the shape of a 3-spoked to 5-spoked wheel or of a rosette which have wall thicknesses of from 0.5 to 4 mm and a diameter of from 3 to 20 mm.

The catalytically active materials of the stated general formula can be prepared in a conventional and known manner by mixing aqueous solutions of, preferably, readily decomposable salts of the components, evaporating down the mixture and/or spray drying, if necessary carrying out compaction and if necessary carrying out multistage calcination, generally at from 250° to 700° C., preferably in two stages at from 250° to 400° C. and from 480° to 660° C., and milling to particle sizes which are in general from 0.1 to 300 μm, preferably from 0.2 to 150 μm, in particular from 0.5 to 50 μm. It is particularly advantageous if iron molybdate gel or bismuth tungstate in dried, powder form is used for the preparation of the catalysts. A gel of this type can be prepared, for example, as described in British Patents 1,282,949 and 1,282,950. The content of bismuth and tungsten in the catalytically active material can be added to the mixture of the water-soluble salts of the other components in the form of bismuth tungstate. In the preparation of the novel catalyst particles, the catalytically active material of the stated general formula may furthermore be diluted with carriers such as kieselguhr, colloidal silica (silica sol) or finely divided titanium dioxide in a conventional manner, the amount of such carriers being not more than 50 parts by weight per 100 parts by weight of catalytically active material. In general, however, it is preferable to use a slightly diluted catalytically active material for the preparation of the novel catalyst particles.

For the preparation of the novel catalyst particles, the powdered catalytically active material, which may be calcined or uncalcined, if necessary finely divided carrier, molding assistants, such as stearic acid, carbon black and melamine, and water (in general from 100 to 500 parts per 100 parts of solids) are generally converted into a pasty material, from which the shapes are formed, for example by extruding and cutting off slices of the extrudate. The novel catalyst particles may also be produced from the catalytically active material and, if required, additives of the stated type by pressing. After the shaping procedure, calcination can be carried out in a conventional manner. The novel catalyst particles have particularly high volume-specific activity and selectivity and high mechanical stability, especially in the gas-phase oxidation of propylene to acrolein and of acrolein to acrylic acid. When used in practice for the gas-phase oxidation or for the gas-phase ammonoxidation, in particular of propylene, but also for the gas-phase oxidation of isobutylene to methacrolein and of methacrolein to methacrylic acid, a particularly small pressure drop occurs in the reactors and the temperature variation is optimized by improved fluidization of the reaction phase. When the novel catalyst particles are used, it is therefore possible to employ reaction tubes having a relatively large free diameter and catalyst particles having relatively large external dimensions, without excessively high hot spots forming as a result of poor removal of heat. The novel catalyst particles also have an improved catalyst life.

BRIEF DESCRIPTION OF THE DRAWINGS

The novel catalyst particles are shown by way of example in FIG. 1, (a) to (c) being 3-spoked to 5-spoked wheels, FIGS. (e) and (d) showing rosettes without spokes and FIGS. d' and e' showing rosettes with spokes.

In the Examples which follow, parts are by weight. Parts by volume bear the same relation to parts by weight as that of the liter to the kilogram.

EXAMPLE 1

A catalytically active material of the general formula

Figure 1A:
Figure 1B:
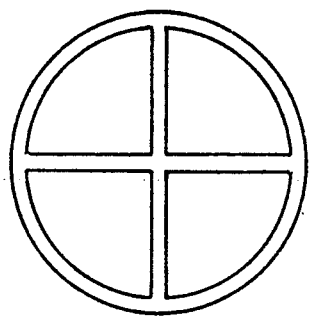
Figure 1C:
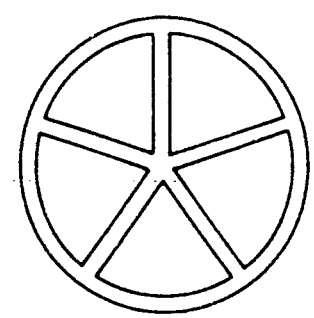
Figure 1D:
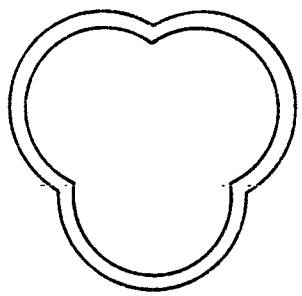
Figure 1D:
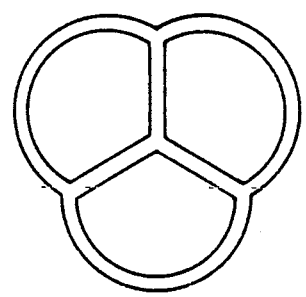
Figure 1E:
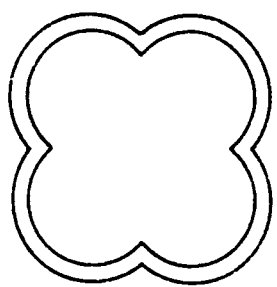
Figure 1E:
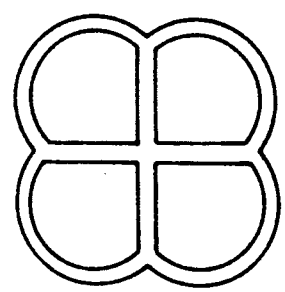
Figure 2A:
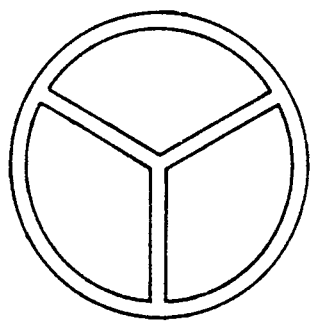
FIG. 2 shows the diameter and wall thicknesses of the wheels and rosettes and the internal diameter of the rosettes schematically. In the case of the rosettes, the ratio of diameter to internal diameter should in general be from 4:1 to 1.2:1, preferably from 2:1 to 1.5:1.
Figure 2B:
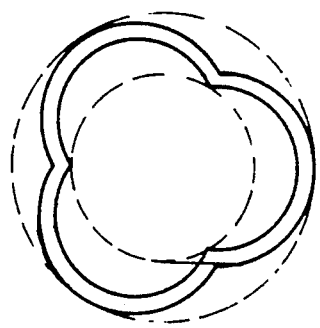

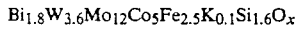
$Bi_{1.8}W_{3.6}Mo_{12}Co_5Fe_{2.5}K_{0.1}Si_{1.6}O_x$ is prepared as described in Example 1 of German Laid-Open Application DOS 3,338,380, dried, and milled to a particle size of 50 μm. 20 parts of water are then added per 100 parts of this catalytically active material, the mixture is kneaded to give a paste and the latter is extruded to produce 3-spoked wheels (corresponding to FIG. 1a) having a diameter of 5 mm and a wall thickness of 1 mm. The catalyst particles are then dried and are heated at 450° C. for 6 hours.

40 parts of the resulting catalyst are introduced into a reactor which is heated by means of a salt bath and has an internal tube diameter of 12 mm. The reactor is charged with a mixture of 4 parts by volume of propene per hour, 36 parts per volume of air per hour and 40 parts by volume of nitrogen per hour, at a salt bath temperature of 360° C. The resulting propene conversion is 95 mol % and the resulting yield of acrolein and acrylic acid together is 89 mol %.

COMPARATIVE EXAMPLE 1

The procedure described in Example 1 is followed, except that the catalyst material which has been converted into a paste is molded to give rings having an external diameter of 5 mm and a wall thickness of 1 mm. Under otherwise identical conditions, the resulting propene conversion in the reactor is 95 mol % and the resulting yield of acrolein and acrylic acid together is only 86.6 mol %.

EXAMPLE 2

1,000 parts of the catalyst prepared as described in Example 1 are introduced into a reactor having a free tube diameter of 25 mm. The salt bath is then heated to 320° C. and 120 parts by volume of propene per hour, 1,080 parts by volume of air per hour and 1,200 parts by volume of an inert gas (N₂) per hour are passed over the catalyst. The pressure at the reactor inlet is 1.6 bar and the resulting propene conversion is 98 mol %. The yield of acrolein and acrylic acid together is 91.5 mol %.

EXAMPLE 3

As described in Example 1, 3-spoked wheels having an external diameter of 5 mm and a wall thickness of 1 mm are produced from catalytically active material of the general formula

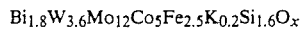
$Bi_{1.8}W_{3.6}Mo_{12}Co_5Fe_{2.5}K_{0.2}Si_{1.6}O_x$ and these wheels are heated as described in Example 1.

50 parts of these catalyst particles are introduced into a reactor heated in a salt bath and having an internal tube diameter of 12 mm. At a salt bath temperature of 360° C., a mixture of 4 parts by volume of propene per hour, 36 parts by volume of air per hour and 40 parts by volume of nitrogen per hour is passed over the catalyst bed. The resulting propene conversion is 95 mol % and the yield of acrolein and acrylic acid together is 89 mol %.

EXAMPLE 4

As described in Example 1, 3-spoked wheels having an external diameter of 5 mm and a wall thickness of 1 mm are produced from catalytically active material of the general formula

$Bi_{1.8}W_{3.6}Mo_{12}Co_5Fe_{2.5}K_{0.4}Si_{1.6}O_x$ and these wheels are heated as described in Example 1.

50 parts of these catalyst particles are introduced into a reactor heated in a salt bath and having an internal tube diameter of 12 mm. At a salt bath temperature of 360° C., a mixture of 3.8 parts by volume of propene per hour, 34.2 parts by volume of air per hour and 38 parts by volume of nitrogen per hour is passed over the catalyst bed. The resulting propene conversion is 95 mol % and the yield of acrolein and acrylic acid together is 89 mol %.

We claim:

1. A catalyst particle of an active material of the formula

$X_{12}Bi_aY_bZ_cA_dE_eG_fO_x,$ wherein
X is selected from the group consisting of Mo, V, W and mixtures thereof,
Y is selected from the group consisting of Fe, Ce and mixtures thereof,
Z is selected from the group consisting of Ni, Co, Zn and mixtures thereof,
A is one or more alkali metals,
E is selected from the group consisting of P, As, Sb, B and mixtures thereof,
G is selected from the group consisting of Si, Al, Ti and mixtures thereof,
wherein
a is from 0.1–5,
b is from 0.1–10,
c is from 1–15,
d is from 0.01–2,
e is from 0–2,
f is from 0–30, and
x is the number of oxygen atoms required to saturate the valences of the other components, wherein said particle has the shape of a 3-spoked to 5-spoked wheel, or of a rosette, each of which have wall thicknesses of from 0.5–4 mm and a diameter of from 3–20 mm.

* * * * *